(12) United States Patent
Lauer (10) Patent No.: US 10,054,655 B2
(45) Date of Patent: Aug. 21, 2018

(54) METHOD AND APPARATUS FOR THE REPRESENTATION OF MAGNETIC RESONANCE DATA

(71) Applicant: Siemens Healthcare GmbH, Erlangen (DE)

(72) Inventor: Lars Lauer, Neunkirchen (DE)

(73) Assignee: Siemens Healthcare GmbH, Erlangen (DE)

( * ) Notice: Subject to any disclaimer, the term of this patent is extended or adjusted under 35 U.S.C. 154(b) by 25 days.

(21) Appl. No.: 15/241,109

(22) Filed: Aug. 19, 2016

(65) Prior Publication Data

US 2017/0052240 A1 Feb. 23, 2017

(30) Foreign Application Priority Data

Aug. 19, 2015 (DE) ........................ 10 2015 215 778

(51) Int. Cl.
*G06K 9/00* (2006.01)
*G01R 33/56* (2006.01)
(Continued)

(52) U.S. Cl.
CPC .......... *G01R 33/5608* (2013.01); *A61B 5/055* (2013.01); *G06T 17/005* (2013.01);
(Continued)

(58) Field of Classification Search
CPC .. A61B 2576/00; A61B 5/055; G01R 33/546; G01R 33/5608; G06F 19/3406;
(Continued)

(56) References Cited

U.S. PATENT DOCUMENTS

2008/0008366 A1 1/2008 Desh et al.
2012/0147010 A1* 6/2012 Schmidt ............... G06F 19/321
345/440

FOREIGN PATENT DOCUMENTS

WO WO-2014047326 A1 3/2014

OTHER PUBLICATIONS

Liu, Manhua, et al. "Identifying informative imaging biomarkers via tree structured sparse learning for AD diagnosis." Neuroinformatics 12.3 (2014): 381-394. (Year: 2014).*

(Continued)

*Primary Examiner* — Nirav G Patel
(74) *Attorney, Agent, or Firm* — Schiff Hardin LLP (57) ABSTRACT

In a method and computer for the representation of magnetic resonance data, and a method and computer for storing magnetic resonance data in a computer, magnetic resonance data are acquired from an object under investigation, the acquired data represents a spatially resolved distribution of values of a number of tissue parameters in the object. A tree structure is created that has a trunk and a number of first tree elements branching from the trunk. A first tissue parameter among the multiple tissue parameters is assigned to the trunk and a second tissue parameter among the multiple tissue parameters is assigned to the number of first tree elements. The tree structure with respect to the acquired values of the multiple tissue parameters, so an adapted tree structure is compiled. The adapted tree structure is presented for a user on a display monitor.

18 Claims, 6 Drawing Sheets

(51) Int. Cl.
  *G06T 17/00* (2006.01)
  *A61B 5/055* (2006.01)
  *G16H 40/63* (2018.01)
  *G01R 33/54* (2006.01)
  *A61B 5/00* (2006.01)

(52) U.S. Cl.
  CPC .............. *G16H 40/63* (2018.01); *A61B 5/742* (2013.01); *G01R 33/546* (2013.01)

(58) Field of Classification Search
  CPC . G06T 11/003; G06T 17/005; G06T 2200/24; G06T 2207/10088; G06T 2207/30004; G06T 7/0012
  See application file for complete search history.

(56) References Cited

OTHER PUBLICATIONS

Ma et al., "Magnetic Resonance Fingerprinting," Nature, vol. 495, pp. 187-192 (2013).
Van Wijk et al., "The Value of Visualization," IEEE, Minneapolis, USA; Conference Proceedings, pp. 79-86 (2005).
Zhang et al., "DBMap: A Space-Conscious Data Visualization and Knowledge Discovery Framework for Biomedical Data Warehouse," IEEE Transactions on Information Technology in Biomedicine, vol. 8, 343-353 (2004).

\* cited by examiner

METHOD AND APPARATUS FOR THE REPRESENTATION OF MAGNETIC RESONANCE DATA

BACKGROUND OF THE INVENTION

Field of the Invention

The invention concerns a method for the representation of magnetic resonance data, as well as a computer, a magnetic resonance apparatus, a method for storing magnetic resonance data in a computer, and a non-transitory, for implementing the methods.

Description of the Prior Art

In a magnetic resonance apparatus, also called a magnetic resonance tomography system, the body of a person to be examined, in particular a patient, is usually exposed by a basic field magnet to a strong basic magnetic field, for example 1.5 or 3 or 7 tesla. In addition, gradient fields are activated by a gradient coil unit. Radio-frequency pulses, such as excitation pulses, are then emitted by a suitable antenna unit, thereby causing nuclear spins of specific atoms, which are excited resonantly by these radio-frequency pulses, to be flipped by a defined flip angle in relation to the magnetic field lines of the basic magnetic field. Upon relaxation of the nuclear spins, radio-frequency signals, so-called magnetic resonance signals, are emitted, and are received by suitable radio-frequency antennas and then further processed. The desired image data are reconstructed from the raw data acquired in this way.

A specific measurement therefore requires the emission of a specific magnetic resonance sequence, also called a pulse sequence, composed of a series of radio-frequency pulses, for example excitation pulses and refocusing pulses, and gradient fields that are emitted in coordination therewith in different gradient axes along different spatial directions. Chronologically matching readout windows specifying the periods in which the induced magnetic resonance signals are acquired are set.

Magnetic resonance imaging enables the acquisition of a spatially resolved distribution of tissue parameters of an object under investigation. The tissue parameters characterize a physical property of the tissue from which the magnetic resonance signals are acquired. The tissue parameters can quantify a reaction of the tissue of the object under investigation to radio-frequency excitation. In this context, the tissue parameters enable the quantification of measuring conditions, such as parameter settings, adjustment measurements, coil intensities, software versions, or the type of magnetic resonance apparatus.

Different magnetic resonance methods or a combination of method enable the quantification of a number of different tissue parameters of the object under investigation. In one conventional method, the multiple tissue parameters are displayed separately from one another, for example in different image windows.

SUMMARY OF THE INVENTION

An object of the invention is to enable improved representation of a number of tissue parameters acquired by magnetic resonance imaging.

The method according to the invention for the representation of magnetic resonance data includes the following method steps.

Magnetic resonance data are acquired from an object under investigation that represent a spatially resolved distribution of values of a number of tissue parameters in the object under investigation.

A tree structure is generated that has a trunk and a number of first tree elements branching from the trunk. A first tissue parameter among the multiple tissue parameters is assigned to the trunk and a second tissue parameter among the multiple tissue parameters is assigned to the number of first tree elements.

An adaptation of the tree structure with respect to the acquired values of the multiple tissue parameters is implemented in order to compile an adapted tree structure.

The adapted tree structure is displayed for a user on a display screen (monitor).

The acquisition of the magnetic resonance data can be the recording of the magnetic resonance data by a magnetic resonance apparatus or the loading of previously recorded magnetic resonance data from a database. The object under investigation can be a patient, a healthy test subject, an animal, or a phantom.

Possible tissue parameters for the multiple tissue parameters are a T1 value (T1 relaxation time), a T2 value (T2 relaxation time), a diffusion value (for example an apparent diffusion coefficient, ADC), a magnetization torque, a proton density, an extracellular volume, a resonance frequency, a concentration of a substance, etc. Other tissue parameters that are considered reasonable to those skilled in the art are also conceivable. Any combination can be determined from the cited tissue parameters. The number of tissue parameters is determined from the same object under investigation, preferably from the same region under investigation. The number of tissue parameters can be determined in a single examination of the object under investigation by operation of the magnetic resonance apparatus.

A quantitative magnetic resonance method can be used to acquire the number of tissue parameters. For example, a T1 mapping (or T2 mapping) method known to those skilled in the art can be used to determine a spatially resolved distribution of the T1 value (or T2 value) in the object under investigation. The use of a magnetic resonance fingerprinting method enabling the simultaneous determination of the spatially resolved distribution of the values of the multiple tissue parameters has been found to be particularly advantageous. One possible magnetic resonance fingerprinting method is known from the publication of Ma et al., "Magnetic Resonance Fingerprinting", Nature, 495, 187-192 (14 Mar. 2013). In this way, the suggested adapted tree structure can be established as a particularly advantageous possibility for the representation of magnetic resonance data obtained by a magnetic resonance fingerprinting method. The suggested adapted tree structure can be used particularly advantageously in a routine workflow in an observation of magnetic resonance data obtained by means of a magnetic resonance fingerprinting method, for example in order to obtain a first overview of the values of the different tissue parameters of the object under investigation.

The values of the multiple tissue parameters represent absolute physical variables. Hence, a value for a tissue parameter is directly related to a physical measured value. The value of the tissue parameter at a specific location can have a physical unit. Hence, it is possible to use various quantitative magnetic resonance methods, possibly under different measuring conditions, to compare different types of magnetic resonance data directly with each another.

The inventive procedure can be used to display values of a number of tissue parameters acquired by magnetic resonance imaging on the display monitor particularly efficiently and/or in a way that is particularly easy for an observer to understand. In this context, the inventive method of representation is fundamentally different from conventional display methods such as a display in gray scales or with color coding, a histogram display, a point cloud display or a combination of such display methods.

Instead, the tree structure in accordance with the invention offers an intuitive format, with unlimited dimensionality, for displaying the values of the multiple tissue parameters. The inventive tree structure is able to display combinations of the values of the multiple tissue parameters, which are acquired by the same image voxel and/or image pixel region under investigation in the examined object. The display of the values of the multiple tissue parameters in the adapted tree structure should take place independently, i.e. no longer spatially resolved. Therefore, the adapted tree structure no longer enables information on the spatial distribution of the values of the multiple tissue parameters to be derived. Instead, the adapted tree structure enables a display of the values of the multiple tissue parameters, in particular a display of a distribution of the values of the multiple tissue parameters in various value ranges and/or value spaces.

The creation of the tree structure can be the construction and/or loading of a generic tree structure, in particular a basic topology for the tree structure. In this context, the tree structure can be created with reference to the selected number of tissue parameters. In this way, the tree structure created exclusively reflects a basic construction of the tree structure, for example a number of dimensions of the tree structure. The actual measured values of the number of tissue parameters from the object under investigation are no longer incorporated during the creation of the tree structure, but only on the adaptation of the tree structure.

During the creation of the tree structure, it is possible to define which tissue parameters among the multiple tissue parameters are assigned to which dimensions of the tree structure, and hence which dimensions of the tree structure represent which tissue parameters among the multiple tissue parameters. The assignment of the first tissue parameter to the trunk can mean that the trunk of the tree structure represents the first tissue parameter. The assignment of the second tissue parameter to the number of first tree elements, can mean that the number of first tree elements represents the second tissue parameter. In this context, the number of first tree elements can be arranged, for example, as branches branching from the trunk. In this way, both the trunk and the number of first tree elements each represent one tissue parameter among the multiple tissue parameters, i.e. a quantitative dimension in each case. Still further tree elements, which in turn branch from the first tree elements in the tree structure, are conceivable. These further tree elements can be embodied, for example, as leaves arranged on the first tree element or as side branches branching from the first tree element. The further tree elements can in turn represent a further tissue parameter among the multiple tissue parameters, i.e. a further quantitative dimension. Alternatively, the further tree elements can also, for example according to their positioning, only represent values of the first tissue parameter and/or of the second tissue parameter.

Accordingly, the tree structure created initially only represents the basic construction of the tree structure, for example which tissue parameter among the multiple tissue parameters should be assigned to which dimension of the tree structure. Therefore, the tree structure created will then be adapted with reference to the values of the multiple tissue parameters actually acquired from the object under investigation. The tree structure adapted in this manner can in this way depict a representation of the measured values of the multiple tissue parameters from the object under investigation.

The adaptation of the tree structure can take place according to an algorithm, wherein the tree structure created and the spatially resolved distribution of the values of the multiple tissue parameters are used as input parameters of the algorithm and the adapted tree structure is the output parameter of the algorithm. In this context, this reflects the spatially resolved distribution of the values of the multiple tissue parameters in one form of the adapted tree structure. Hence, different values of the number of tissue parameters lead to different forms of the adapted tree structure.

Possibilities for the adaptation of the tree structure with reference to the values of the number of tissue parameters include the definition of a number of the plurality of first tree elements, the definition of positions on the trunk from which the number of first tree elements branch off, the definition of a thickness of the trunk and/or the number of first tree elements, etc. In each case an arrangement of the tree elements of the next higher dimension on the tree elements of the lower dimension can encode the values of the multiple tissue parameters of the lower dimension in the adapted tree structure. Various possibilities for the adaptation of the tree structure are described below with reference to the values of the multiple of tissue parameters.

Since values of a number of tissue parameters are to be acquired from the same object under investigation, it is advantageous that, also from the same region under investigation, multiples of the values of various tissue parameters, which are acquired from the same position in the object under investigation. These multiples of the values of the various tissue parameters contain the same positional information. For example, a first value of a first tissue parameter, a second value of a second tissue parameter and a third value of a third tissue parameter can be acquired by the same image pixel or image voxel. The first value, second value and third value can then form a multiple of this kind. These associated multiples with respect to the spatially resolved distribution of the values of the various tissue parameters can then be used to adapt the tree structure.

The display of the adapted tree structure on the display monitor can be combined with a two-dimensional or three-dimensional map reflecting the spatially resolved distribution of the values of at least tissue parameter out of the number of tissue parameters. A combined display of this kind is described in more detail below. The adapted tree structure can also be displayed separately or individually on the display monitor. The user can observe the adapted tree structure displayed on the display monitor. The adapted tree structure can be displayed on the display monitor in the form of a tree with a trunk and branches branching from the trunk. Any abstracted display that appears advisable to those skilled in the art is also possible, wherein the abstracted display depicts the trunk and the multiple first tree elements branching from the trunk.

The user can derive valuable information on the distribution from the values of the multiple tissue parameters and hence valuable diagnostic information with respect to the object under investigation from the tree structure displayed. The appearance or a model of the adapted tree structure displayed can be used to determine anomalies in the value distribution of the multiple tissue parameters of the object under investigation in a relatively simple or intuitive manner. In this way, the inventive adapted tree structure enables the efficient and easy-to-understand visualization of the multidimensional tissue parameters.

The adapted tree structure offers a user observing the structure, for example a radiologist, a familiar structure, in particular a structure known from nature. This provides the observer with rapid access to this new type of display quickly. The adapted tree structure offers a drastically simplified display of the multidimensional values of the plurality of tissue parameters. The suggested display enables the user to recognize complex relationships between the values of the various tissue parameters intuitively. Specific combinations of tissue parameter can be visually identified in a particularly simple manner and as described below in more detail selected or marked by the user in a particularly simple manner.

In an embodiment, the tree structure is adapted such that the trunk is assigned a value scale representing values of the first tissue parameter, wherein the multiple first tree elements are arranged along the value scale in accordance with the acquired values of the first tissue parameter.

The value scale can be arranged along the trunk. The value scale includes a physical unit corresponding to the physical unit of the first tissue parameter. The value scale can be displayed to the user on the display monitor together with the adapted tree structure. Alternatively, the value scale can only be used for the adaptation of the tree structure and hidden from the user. The value scale can extend, for example, along the entire trunk, i.e. start at a base at which the trunk starts and finish at an endpoint at which the trunk finishes. The value scale can alternatively only extend along only a part of the trunk. In this way, the value scale can be arranged along the trunk such that the values of the value scale increase as the distance from the base increases.

In the same way, the first tree element, which is then embodied as a branch that branches from the trunk, can be assigned a further value scale representing values of the second tissue parameter. A number of further tree elements, for example leaves or branches, can then be arranged in the same way on the first tree elements in accordance with the acquired values of the second tissue parameter along the further value scale. This procedure can be continued similarly for any value parameter dimension.

The arrangement of the multiple first tree elements along the value scale according to the first values of the first tissue parameter can mean that the first tree elements branch from the trunk at places along the value scale branching from the trunk are defined by the values of the first tissue parameter. For example, the distance of a branch fork from the base can represent at least one data value of the first tissue parameter. In the same way, a data value of the second tissue parameter can be encoded by a distance of an arrangement of a further tree element, for example a further branch or leaf, from the branch fork.

In one conceivable, although possibly unclear, display option, a first tree element among the multiple first tree elements can branch from the trunk at the respective place according to the value scale for each value of the first tissue parameter. For a quantity among a number of similar values of the first tissue parameter, it is possible for only one first tree element among the multiple first tree elements to branch from the trunk as is described in more detail with reference to the following embodiment.

In this embodiment, a first value range of the first tissue parameter is defined, and the tree structure is adapted such that a first tree element among the multiple first tree elements is assigned to the first value range.

The first value range can contain a quantity among a number of values, in particular similar values or values which are very close together, of the first tissue parameter. The combination of a number of values of the first tissue parameter to form in each case a first tree element among the multiple first tree elements can greatly improve the clarity of the display.

As is described in more detail with reference to the following embodiment, in this context, a thickness of the first tree element can represent a number of values, which are contained in the quantity of the values of the first tissue parameter. As will be described in more detail below, a position on the trunk at which the first tree element branches from the trunk can be set with reference to the first value range.

In this embodiment, the tree structure is adapted such that an expansion of the first tree element is dependent on a number of voxels of the magnetic resonance data for which the value of the first tissue parameter lies within the first value range.

The expansion of the tree element can be, for example, a thickness of a branch or a size of a leaf. The more voxels (or image voxels/pixels) with a value of the first tissue parameter within the first value range comprised by the magnetic resonance data, the greater the expansion of the first tree element can be selected.

It is also possible for the expansion of a second tree element branching from the first tree element to be selected with reference to a number of voxels in a second value range of the second tissue parameter. In principle, the expansion of the second tree element can then be smaller than the expansion of the first tree element since the only voxels represented by the second tree element are those for which the value of the first tissue parameter lies within in the first value range and for which the value of the second tissue parameter simultaneously lies within the second value range. In the case of multidimensional tissue parameter sets, this advantageously enables the thickness of branching branches to represent the number of data points comprising a specific combination of tissue parameters.

In another embodiment, the tree structure is adapted such that a position on the trunk at which the first tree element branches from the trunk is set with reference to the first value range.

This enables the first tree element to branch at a place along the value scale that is defined by the first value range. The position on the trunk from which the first tree element branches can then be defined from the quantity among the number of values of the first tissue parameter in the first value range, for example a focus and/or a median value and/or a mean value of the quantity among the multiple of values of the first tissue parameter.

In this case it is conceivable for the trunk to have a number of prespecified positions assigned to different value ranges. The first tree element can then be arranged at the position among the number of prespecified positions that is assigned to the first value range.

In another embodiment, the tree structure is adapted such that a thickness of the trunk of the adapted tree structure reflects a number of all the image points of the spatially resolved distribution of the values of the number of tissue parameters.

With this optional display variant, the thickness of the trunk can be specified by the total number of voxels or pixels of the magnetic resonance data (for example 262144 voxels or pixels with a 512×512 matrix).

In another embodiment, the number of first tree elements are embodied as branches branching from the trunk and the tree structure has a number of second tree elements branching from the first tree elements.

In this context, a third tissue parameter among the multiple tissue parameters can be assigned to the number of second tree elements. In this case, the number of second tree elements is embodied as branches that branch from the number of first tree elements.

It is alternatively possible for the number of second tree elements to be embodied as leaves and, by virtue of their positioning on the number of first tree elements, only to represent values of the second tissue parameter. Then no further tissue parameter is assigned to the plurality of second tree elements.

Those skilled in the art can will recognize that this concept can be continued for any number of tree elements. In this way, the values of multidimensional tissue parameters can be displayed in abstracted form in the adapted tree structure.

In another embodiment, one specific tissue parameter among the multiple tissue parameters is assigned a plurality of tree elements in the highest hierarchical level of the tree structure, wherein leaves representing values of the specific tissue parameter are arranged on this number of tree elements.

Therefore, the tree has a number of hierarchical levels, wherein each hierarchical level is assigned one tissue parameter out of the plurality of tissue parameters. In this context, the trunk to which the first tissue parameter is assigned forms the first hierarchical level. The number of first tree elements to which the second tissue parameter is assigned forms the second hierarchical level, etc. No tree elements to which further tissue parameter are assigned branch from the highest hierarchical level to which the specific tissue parameter among the multiple of tissue parameters is assigned.

The leaves arranged on the number of tree elements in the highest hierarchical level are defined such that no further tree elements branch therefrom. The leaves themselves do not represent any tissue parameter among the multiple tissue parameters.

The positioning of the leaves on the number of tree elements in the highest hierarchical level can instead represent the values of the specific tissue parameter. For example, the number of tree elements can in each case be assigned a value scale representing values of the specific tissue parameter, wherein the number of leaves is arranged along the value scale in accordance with the acquired values of the specific tissue parameter. In this context, a leaf can be assigned to a value range of the specific tissue parameter. An expansion or size of the leaf can then be dependent upon a number of voxels of the magnetic resonance data with a value of the specific tissue parameter lying within this value range.

In another embodiment, the adapted tree structure is displayed on a user interface, and the user interacts with the adapted tree structure via the user interface.

The interaction of the user with the adapted tree structure can take place by an interaction element on the user interface, for example a button, a slider control, a movement of the cursor. The user can also interact directly with the adapted tree structure by parts of the tree structure, for example the trunk and/or tree elements, being embodied directly as interaction elements with which the user is able to interact.

The interaction can provide the user with the possibility of modifying the adapted tree structure as desired so that it is even more informative to the user. It is also possible for the user to use the interaction to select specific combinations of tissue parameters to be displayed in the adapted tree structure or in a spatially resolved image display of the magnetic resonance data. Various possibilities for the interaction of the user with the adapted tree structure are described in the following embodiments. Further interactions of the user with the adapted tree structure that appear advisable to those skilled in the art can also be implemented.

In another embodiment, the interaction of the user with the adapted tree structure includes the selection of tissue parameters to be displayed among the multiple tissue parameters by the user, and the adapted tree structure is modified with reference to the selection of the tissue parameter to be displayed and displayed in modified form on the display monitor.

In this way, the user can select that only a subset of the tissue parameters acquired from the object under investigation should be represented by the trunk or the tree elements of the modified tree structure. For example, the user can be provided with the possibility of selectively choosing tissue parameters to be displayed in the modified tree structure that are of particular interest to the user for a specific application. When the values of numerous different tissue parameters have been acquired from the object under investigation, it can be advisable to provide the user with the possibility of restricting the tissue parameters for display in the modified tree structure so that the modified tree structure can represent the values of the tissue parameters of interest to the user in a particularly clear way.

In another embodiment, the adapted tree structure is displayed on the user interface together with a spatially resolved image display of the magnetic resonance data.

The spatially resolved image display of the magnetic resonance data can be a display of a two-dimensional or three-dimensional map of the values of the multiple tissue parameters. In this context, it is possible for a separate map to be displayed for each tissue parameter out of the plurality of tissue parameters. It is also possible for a number of tissue parameters to be displayed combined in one map, for example by the use of different colors.

The adapted tree structure can be displayed on the user interface in the same window as the spatially resolved image display of the magnetic resonance data. The adapted tree structure can also be displayed in a separate window. As described in more detail below, it is advantageous for the display of the adapted tree structure to be linked to the spatially resolved image display of the magnetic resonance data. This means that interaction with the adapted tree structure can have an impact on the spatially resolved image display of the magnetic resonance data, or vice versa.

This inventive procedure can be used to display the values of the multiple tissue parameters simultaneously in the display of the tree structure and in the conventional spatially resolved image display.

One embodiment provides that the interaction of the user with the adapted tree structure includes the selection of a tree element of the tree structure, wherein the data points belonging to the tree element data points are highlighted in the spatially resolved image display of the magnetic resonance data.

The selection of the tree element of the tree structure can be, for example, a selection of the trunk or of at least one (side) branch or of at least one leaf of the tree structure. The user can select the respective tree element by clicking the mouse on the respective tree element. This enables the user to select specific combinations of tissue parameters in the adapted tree structure intuitively and particularly quickly.

The data points belonging to the tree element are the image pixels or voxels of the magnetic resonance data representing values of the number of tissue parameters represented by the tree element. This enables the image pixels or voxels belonging to the selected tree element to be displayed in the spatially resolved display. For example, it is conceivable for the user to select a location in the adapted tree structure that appears suspicious or relevant to diagnosis and to see the associated structures directly in the spatially resolved image display. The associated data points can be highlighted by the coloration or brightening of the associated data points.

In another embodiment, a selection of a data point in the spatially resolved image display of the magnetic resonance data on the user interface results in the highlighting of a tree element of the tree structure belonging to the data point in the adapted tree structure.

The highlighting of the associated tree element can be implemented, for example, by the coloration or brightening of the associated tree element. In particular the tree element that is highlighted in the adapted tree structure can be the tree elements that represents the values of the multiple tissue parameters of the selected data point. The possibility of this selection of the data point can be offered to the user separately or in addition to the selection of the tree element described with respect to the preceding embodiment.

In another embodiment, at least one tissue parameter among the multiple tissue parameters is selected from the following list: a value for a proton density, a T1 value, a T2 value, a diffusion value, a value of an extracellular volume.

These tissue parameters represent particularly advantageous quantitative parameters, which can be acquired by magnetic resonance imaging from the object under investigation. Other tissue parameters that can be quantified by magnetic resonance imaging and that appear advisable to those skilled in the art are also conceivable.

The computer according to the invention has a data acquisition unit, a creation unit, an adaptation unit and a display monitor, wherein the computer is embodied to carry out a method according to the invention.

The computer according to the invention is configured to carry out a method for displaying magnetic resonance data. The data acquisition unit is configured for the acquisition of magnetic resonance data of an object under investigation comprising a spatially resolved distribution of values of a number of tissue parameters in the object under investigation. The creation unit is configured for the creation of a tree structure comprising a trunk and a number of first tree elements branching off from the trunk, wherein a first tissue parameter among the multiple tissue parameters is assigned to the trunk and a second tissue parameter among the multiple tissue parameters is assigned to the number of first tree elements. The adaptation unit is configured for the adaptation of the tree structure with reference to the acquired values of the plurality of tissue parameters, wherein an adapted tree structure is compiled. The display monitor is configured to display the adapted tree structure for a user.

The magnetic resonance apparatus according to the invention has a computer according to the invention. The computer can be configured to send control signals to the magnetic resonance apparatus and/or to receive and/or process control signals in order to carry out the method according to the invention. The computer can be integrated in the magnetic resonance apparatus. The computer can also be installed separately from the magnetic resonance apparatus.

The computer can be connected to the magnetic resonance apparatus. The acquisition of the magnetic resonance data can be a recording of magnetic resonance data by a scanner unit of the magnetic resonance apparatus. The magnetic resonance apparatus can then transmit the magnetic resonance data to the computer. The computer can then acquire the magnetic resonance data by operation of the data acquisition scanner.

A first non-transitory, computer-readable storage medium according to the invention can be loaded directly into a memory of a programmable computer and is encoded with program code for carrying out the above-described method according to the invention for displaying magnetic resonance data when the program code of the first storage medium is executed in the computer. This enables the method according to the invention to be carried out quickly, identically repeatedly and robustly. In this context, the computer must in each case fulfill the requisite conditions such as, for example, having an appropriate random access memory, an appropriate graphics card or an appropriate logic unit so that the respective method steps can be carried out efficiently.

Examples of electronically readable data media are a DVD, a magnetic tape or a USB stick on which electronically readable control information, in particular software (see above), is stored.

The method according to the invention for storing magnetic resonance data in a computer has the following steps.

Magnetic resonance data are acquired from an object under investigation that represent a spatially resolved distribution of values of a number of tissue parameters in the object under investigation. The multiple tissue parameters include a first tissue parameter and a second tissue parameter, wherein a first value of the first tissue parameter and a second value of the second tissue parameter are assigned to a first item of location information.

A data structure is created in the form of a structure having a trunk and a number of first tree elements branching from the trunk, and the first tissue parameter is assigned to the trunk and the second tissue parameter is assigned to the number of first tree elements.

The adaptation of the data structure with respect to the acquired values of the multiple tissue parameters, wherein an adapted data structure is compiled.

The first item of location information is stored at a point in the adapted data structure that is defined with respect to the first value of the first tissue parameter and the second value of the second tissue parameter.

The first positional information can be specified by two-dimensional or three-dimensional spatial coordinates. The fact that the first value of the first tissue parameter and the second value of the second tissue parameter are assigned to the first item of location information then means that the first value was measured at the spatial coordinates for the first tissue parameter and the second value was measured at the spatial coordinates for the second tissue parameter.

The data structure in the form of the tree structure can be created and adapted in a similar way to the tree structure described above, which is provided to display the magnetic resonance data. The data structure is only created and adapted on the computer in the form of the tree structure. In this way, possibly contrary to the case described above, the tree structure can be implemented in a greatly abstracted way on the computer with respect to the display of the magnetic resonance data.

Contrary to the conventional case in which the values of the multiple tissue parameters are stored with respect to the spatial coordinates, for example in the form of a two-dimensional or three-dimensional matrix, the tree structure in accordance with the invention offers a completely new type of data model for storing the magnetic resonance data.

Instead of the conventional storage, the tree structure enables the positional information, i.e., for example, the spatial coordinates, to be stored in the tree structure, which is adapted with respect to the actually measured values of the tissue parameters. For example, the first item of positional information can be stored in a leaf of the adapted tree structure, namely on the leaf of the adapted tree structure representing the first value of the first tissue parameter and the second value of the second tissue parameter. This enables a number of items of spatial information from various data points to be stored on one leaf of the tree structure.

The entries in the data structure are then no longer the values of the tissue parameters, but are the spatial coordinates at which specific combinations of values of the tissue parameters were measured. The data structure is constructed in the form of the tree structure with reference to the values of the multiple tissue parameters.

The storage of the magnetic resonance data in the adapted data structure enables simplified retrieval of the magnetic resonance data to be displayed in the tree structure described above. Data management of this kind can simultaneously enable a more rapid memory access to specific tree elements or sub-areas of the tree structure.

The adapted data structure with the stored first positional information can finally be stored in a database for subsequent retrieval.

The second non-transitory, computer-readable data storage medium according to the invention can be loaded directly into a memory of a programmable computer and has program code for carrying out the method according to the invention for storing magnetic resonance data when the program code is executed in the computer. Further aspects of the second storage medium are analogous to the description of the first storage medium.

The advantages of the computer according to the invention, the magnetic resonance apparatus according to the invention and the first and second storage media according to the invention correspond to the advantages of the methods according to the invention, which were described above in detail. Features, advantages or alternative embodiments mentioned above are also applicable to the other inventive aspects.

DESCRIPTION OF THE PREFERRED EMBODIMENTS

Figure 1:
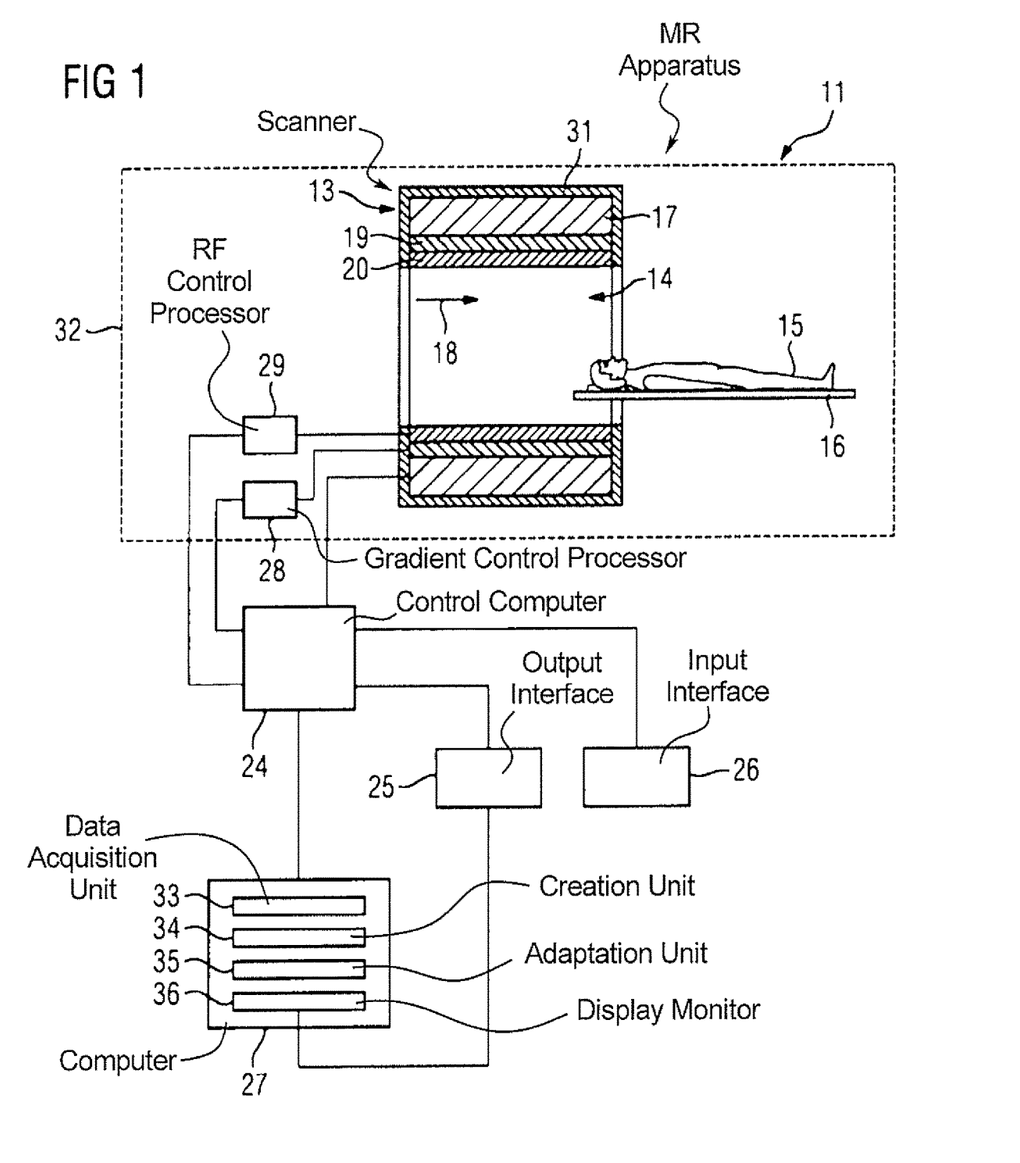
FIG. 1 is a schematic illustration of a magnetic resonance apparatus according to the invention that has a computer according to the invention.

FIG. 1 is block diagram of a magnetic resonance apparatus according to the invention 11 with a computer 27 according to the invention. The magnetic resonance apparatus 11 has a data acquisition scanner 13 having a basic field magnet 17 that generates a strong and constant basic magnetic field 18. The magnetic resonance scanner 13 has a cylindrical patient receiving area 14 for receiving an object 15 under investigation, in the present case a patient, wherein the patient receiving area 14 is cylindrically enclosed in the circumferential direction by the scanner 13. The patient 15 can be moved into the patient receiving area 14 by a patient support 16. The patient support 16 has a table arranged movably inside the scanner 13. The scanner 13 is shielded from the outside by a housing shell 31.

The scanner 13 further has a gradient coil arrangement 19 that generates magnetic field gradients, which are used for spatial encoding during imaging. The gradient coil arrangement 19 is controlled by a gradient control processor 28. The scanner 13 also has a radio-frequency antenna 20, which in the case shown is designed as a body coil permanently integrated in the scanner 13, and a radio-frequency antenna control processor 29 that operates the radio-frequency antenna 20 so as to emit radio-frequency magnetic resonance sequences into an examination chamber, which is substantially formed by the patient receiving area 14. In such a sequence, nuclear spins in the subject are excited by radio-frequency pulses emitted by the radio-frequency antenna 20, which cause certain nuclear spins within the object 15 to be given a magnetization that deviates from the alignment produced by the field lines of the basic magnetic field 18. As these nuclear spins relax following the excitation, they emit magnetic signals. The radio-frequency antenna 20 is further designed to receive the magnetic resonance signals from the patient 15.

To control the basic field magnet 17, the gradient control processor 28 and the radio frequency antenna control processor 29, the magnetic resonance apparatus 11 has a control computer 24. The control computer 24 controls the magnetic resonance apparatus 11 centrally, such as, for example, to perform predetermined imaging gradient echo sequences. Control information such as imaging parameters, and reconstructed magnetic resonance images can be provided to a user on an output interface 25 of the magnetic resonance apparatus 11. The magnetic resonance apparatus 11 also has an input interface 26 via which information and/or parameters can be entered by a user during a measuring process. The control computer 24 can include the gradient control processor 28 and/or the radio frequency antenna control processor 29 and/or the output interface 25 and/or the input interface 26.

The scanner 13 and the radio-frequency control processor and the gradient control processor form a data acquisition unit 32.

The magnetic resonance apparatus 11 can have further components as are common for magnetic resonance apparatuses. The general manner of operation of a magnetic resonance apparatus is known to those skilled in the art so that a detailed description of the further components is not necessary herein.

The magnetic resonance apparatus 11 shown has a computer 27 that has a data acquisition unit 33, a creation unit 34, an adaptation unit 35 and a display monitor 36. This enables the computer 27 to implement a method according to FIG. 2.

When implementing a method according to the invention, the computer 27 loads magnetic resonance data from a database via the data acquisition unit 33. When the method according to the invention is carried out by a combination of the magnetic resonance apparatus 11 and the computer 27, the data acquisition unit 33 of the computer 27 in particular acquires magnetic resonance data recorded by means of the image data acquisition unit 32 of the magnetic resonance apparatus 11. To this end, the data acquisition unit 33 is connected to the computer 24 of the magnetic resonance apparatus 11 for data exchange.

The display monitor 36 of the computer 27 can be connected to the output interface 25 of the magnetic resonance apparatus 11 to display the adapted tree structure at a display screen thereof. The display monitor 36 of the computer 27 can also be connected to other display monitors, which are embodied separately from the magnetic resonance apparatus.

Figure 2:
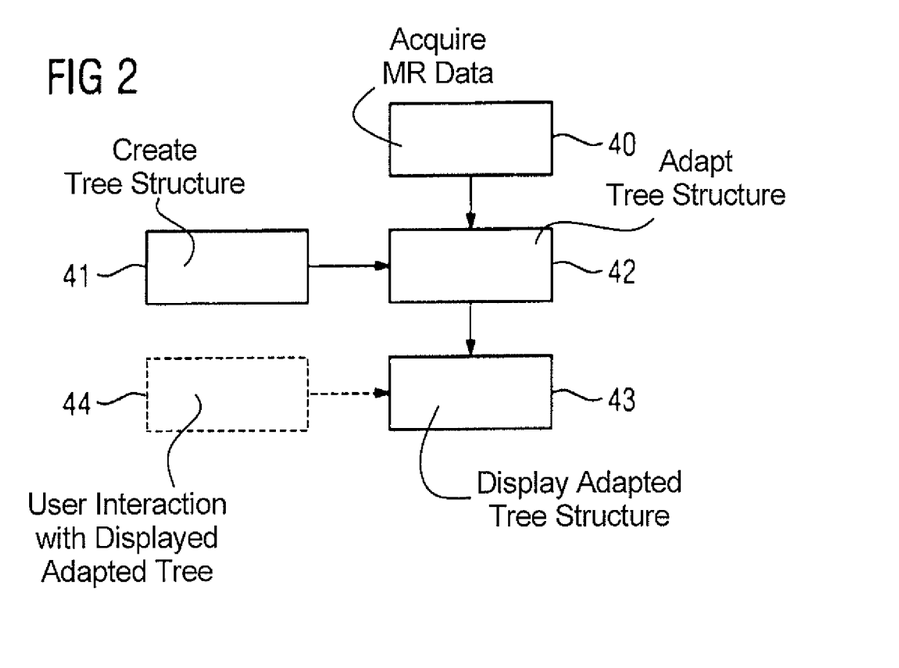
FIG. 2 is a flowchart of an embodiment of the method according to the invention for the representation of magnetic resonance data.

FIG. 2 is a flowchart of an embodiment of the method according to the invention for the representation of magnetic resonance data.

In a first method step 40, magnetic resonance data of an object 15 under investigation 15 are acquired by the scanner 13. The data represent a spatially resolved distribution of values of a number of tissue parameters in the object 15 under investigation.

In a further method step 41, a tree structure is created by the creation unit 34. The tree structure has a trunk and a number of first tree elements branching from the trunk. A first tissue parameter among the multiple tissue parameters is assigned to the trunk and a second tissue parameter among the multiple tissue parameters is assigned to the plurality of first tree elements.

In a further method step 42, the tree structure is adapted with respect to the acquired values of the multiple tissue parameters by means of the adaptation unit 35, so an adapted tree structure is compiled.

In a further method step 43, the display of the adapted tree structure is presented for a user by the display monitor 36. In this context, the display monitor 36 of the computer 27 can be connected to an output unit to display the adapted tree structure.

The adapted tree structure can optionally be displayed on a user interface and, in a further optional method step 44, the user interacts with the adapted tree structure on the user interface. The interaction of the user with the adapted tree structure can include, for example, a selection by the user of those tissue parameters among the multiple tissue parameters to be displayed, and the adapted tree structure is modified with respect to the selection of the tissue parameters to be displayed, and tree structure is displayed in modified form on the display monitor. Other interactions of the user with the adapted tree structure are obviously also conceivable (see for example FIG. 6 or FIG. 7).

The method steps of the method according to the invention shown in FIG. 2 are carried out by the computer 27. To this end, the computer 27 has the necessary software and/or computer programs (program code), which are stored in a memory unit of the computer 27.

Figure 3:
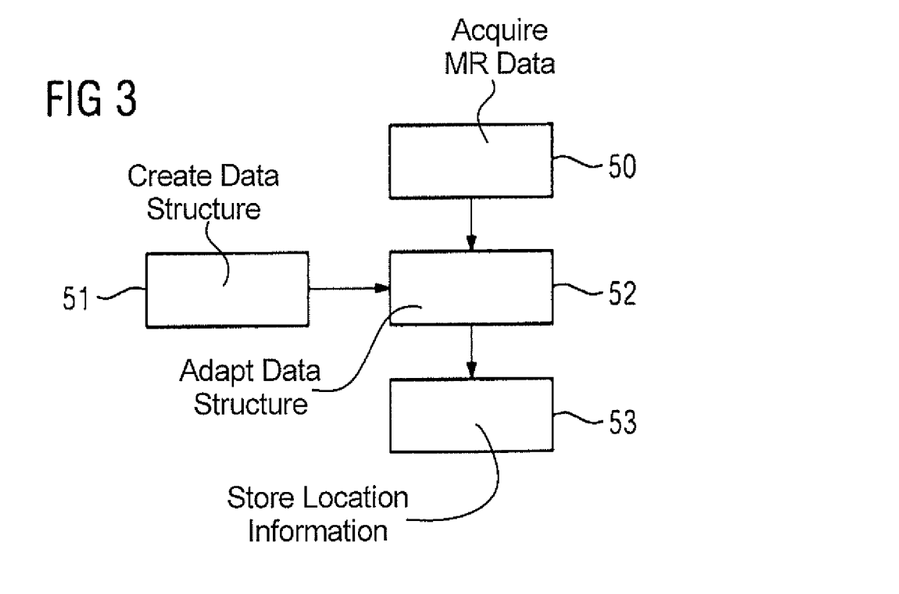
FIG. 3 is a flowchart of an embodiment of the method according to the invention for storing magnetic resonance data in a computer.

FIG. 3 is a flowchart of an embodiment of the method according to the invention for storing magnetic resonance data in a computer.

In a first method step 50, magnetic resonance data of an object 15 under investigation 15 by the scanner 13. The data represent a spatially resolved distribution of values of a number of tissue parameters in the object 15. The multiple tissue parameters include a first tissue parameter and a second tissue parameter, with a first value of the first tissue parameter and a second value of the second tissue parameter being assigned to a first item of location information.

In a further method step 51, a data structure is created that has a trunk and a number of first tree elements branching from the trunk. The first tissue parameter is assigned to the trunk and the second tissue parameter is assigned to the number of first tree elements.

In a further method step 52, the data structure is adapted with respect to the acquired values of the multiple tissue parameters, so an adapted data structure is compiled.

In a further method step 53, the first item of location information is stored at a point in the adapted data structure that is defined with respect to the first value of the first tissue parameter and the second value of the second tissue parameter.

The method steps of the method according to the invention depicted in FIG. 3 can also be carried out by the computer 27. To this end, the computer 27 comprises the necessary software and/or computer programs (program code), which are stored in a memory unit of the computer 27.

Figure 4:
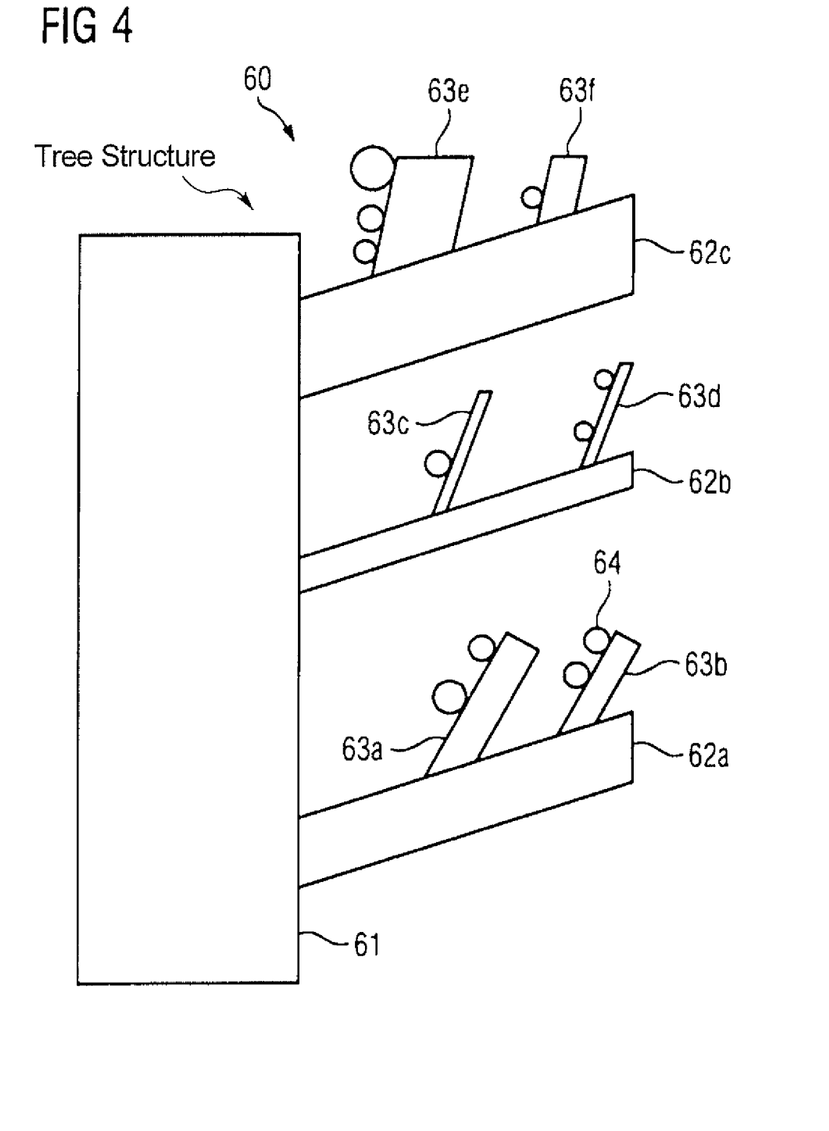
FIG. 4 shows an exemplary tree structure according to the invention, which has been created and adapted to display or store the magnetic resonance data.

FIG. 4 shows an exemplary tree structure according to the invention 60, which has been created to display or store the magnetic resonance data.

In this context, reference is made to the fact that FIG. 4 is only an exemplary depiction of a tree structure 60 that can be displayed by means of the display monitor 36. Those skilled in the art can derive any number of possibilities for a form of the tree structure 60 from the display in FIG. 4. For example, those skilled in the art can vary the number of the tree elements, the thickness of the trunk 61 or the tree elements, the depiction or presence of the leaves and/or the arrangement or alignment of the as desired. For example, the branches branching off from the trunk 61 can also be arranged on the left side or on both sides of the trunk 61. FIG. 4 is only intended to depict one possibility for the appearance of the adapted tree structure 60 in order to explain the invention.

In the case shown in FIG. 4, a spatially resolved distribution of values of three tissue parameters in the object 15 under investigation was acquired. Differing from the case shown in FIG. 4 case, it is also possible for values of two or more than three tissue parameters to be acquired from the object 15. The three tissue parameters can be selected from the following list: a value for a proton density, a T1 value, a T2 value, a diffusion value, a value of an extracellular volume. Obviously, other tissue parameters are also conceivable.

The tree structure 60 has a trunk 61, three first tree elements 62*a*, 62*b*, 62*c*, six second tree elements 63*a*, 63*b*, 63*c*, 63*d*, 63*e*, 63*f* and a number of third tree elements 64. In this context, the number of respective tree elements depicted in FIG. 4 should be considered only to be an example. It is possible for any number of tree elements to be implemented depending on the specific values of the tissue parameters and/or requirements relating to the clarity of the tree structure 60.

In this context, the first tree elements 62*a*, 62*b*, 62*c* are depicted as branches branching from the trunk 61. In this context, the second tree elements 63*a*, 63*b*, 63*c*, 63*d*, 63*e*, 63*f* branch from the first tree elements 62*a*, 62*b*, 62*c* and are in turn embodied as branches. In this context, one part of the second tree elements 63a, 63b branches from a lower first tree element 62a. A further part of the second tree elements 63c, 63d branches from a middle first tree element 62b. In this context, a further part of the second tree elements 63e, 63f branches from an upper first tree element 62c. A different division of the second tree elements 63a, 63b, 63c, 63d, 63e, 63f between the first tree elements 62a, 62b, 62c is also conceivable. The third tree elements 64 are embodied as leaves, which are arranged on the second tree elements 63a, 63b, 63c, 63d, 63e, 63f.

A first tissue parameter of the three tissue parameters is assigned to the trunk 61. A second tissue parameter of the three tissue parameters is assigned to the first tree elements 62a, 62b, 62c. A third tissue parameter of the three tissue parameters is assigned to the second tree elements 63a, 63b, 63c, 63d, 63e, 63f.

The specific adaptation of the tree structure 60 with reference to the acquired values of the three parameters for the creation of the adapted tree structure 60, as is depicted by way of example in FIG. 4, can be performed by a variety of procedures. The respective specific depiction of the tree structure 60 is, therefore, obtained from the values of the three tissue parameters. In this context, parameterization of the tree structure 60 can be specified by the user and/or determined (partially) automatically.

For example, a number or an expansion of the tree elements can be dependent upon the specific values of the three tissue parameters. The assignment of the second tree elements 63a, 63b, 63c, 63d, 63e, 63f to the respective first tree elements 62a, 62b, 62c can also be dependent upon the specific values of the tissue parameters. The position at which the first tree elements 62a, 62b, 62c branch from the trunk 61, or at which the second tree elements 63a, 63b, 63c, 63d, 63e, 63f branch from the first tree elements 62a, 62b, 62c, or at which the third tree elements 64 are arranged on the second tree elements 63a, 63b, 63c, 63d, 63e, 63f, is dependent upon the specific values of the tissue parameters.

In the case shown in FIG. 4, there are a low value range, a middle value range and an upper value range for the first tissue parameter shown as an example. In this context, the low value range, the middle value range and the upper value range are the three first value ranges in the inventive procedure. The tree structure 60 is then adapted, as an example, such that in each case a first tree element 62a, 62b, 62c is assigned to a value range of the three first value ranges. For example, the lower first tree element 62a is assigned to the low value range, the middle first tree element 62b to the middle value range and the upper first tree element 62c to the upper value range.

In this context, the tree structure 60 can be adapted such that an expansion of the first tree elements 62a, 62b, 62c is dependent on a number of voxels of the magnetic resonance data, for which the value of the first tissue parameter lies within the respective value ranges. Since, in the case shown by way of example in FIG. 4, the majority of the values of the first tissue parameter should lie within the upper value range, in the case shown in FIG. 4, the upper first tree element 62c is also the most greatly expanded first tree element 62a, 62b, 62c.

In the same way, the tree structure 60 can be adapted such that a thickness of the trunk 61 of the adapted tree structure 60 reflects a number of all image points of the spatially resolved distribution of the values of the plurality of tissue parameters. It can be identified in FIG. 4 that the expansion of the tree elements decreases with each hierarchical level from the trunk 61. This is due to the fact that, with increasing hierarchical levels, an increasingly small number of image points are present with the respective combinations of the tissue parameters represented by the respective tree elements.

In this context, the tree structure 60 can be adapted such that the positions on the trunk 61, at which the first tree elements 62a, 62b, 62c branch off from the trunk 61 are set with respect to the low value range, the middle value range and the upper value range. For example, the values of the first tissue parameter in the low value range are smaller than the values of the first tissue parameter in the middle value range. In this way, the middle first tree element 62b, which is assigned to the middle value range, is positioned farther away from the base of the trunk 61 than the lower first tree element 62a, which is assigned to the low value range.

The inclusion of the values of the second tissue parameter can be continued in a similar way to the described representation of the values of the first tissue parameter. For example, it is also possible for there to be a number of second value ranges for the second tissue parameter. In the case shown in FIG. 4, there are two items as an example. Then in each case a second tree element 63a, 63b, 63c, 63d, 63e, 63f can be assigned to the respective second value ranges. An expansion of the second tree elements 63a, 63b, 63c, 63d, 63e, 63f can in turn represent a number of voxels of the magnetic resonance data for which the value of the second tissue parameter lies within the respective second value range. The positions on the first tree elements 62a, 62b, 62c at which the second tree elements 63a, 63b, 63c, 63d, 63e, 63f branch from the first tree elements 62a, 62b, 62c can be set with reference to the second value ranges.

Finally, the second tree elements 63a, 63b, 63c, 63d, 63e, 63f can form the tree elements in the highest hierarchical level of the tree structure 60. The third tree elements 64 embodied as leaves, which are arranged on these second tree elements 63a, 63b, 63c, 63d, 63e, 63f, can then represent the values of the third tissue parameter. No tissue parameter is assigned to the actual third tree elements 64. The expansion of the leaves can optionally in turn reflect a number of voxels in respective third value ranges of the third tissue parameter.

Hence, the display in FIG. 4 illustrates a possible concept for the creation or the adaptation of the tree structure 60. In particular, the tree structure 60 depicted enables an effective visualization of combinations of specific values of the three tissue parameters. For example, in the tree structure 60 depicted in FIG. 4, the branch 63f arranged at the top left encodes the values of the first tissue parameter, which lie within the upper value range, and simultaneously the values of the second tissue parameter in a second value range. At the same time, each leaf 64 can simultaneously encode values of all three tissue parameters in the respective value ranges.

Generally, in a possible display it is in each case possible for the tree elements in a hierarchical level to encode a number of values or a size of values of a tissue parameter, which is assigned to the tree elements or the trunk 61 of the next lowest hierarchical level. Accordingly, the trunk 61 does not itself have to encode any values of tissue parameters since there is no level below the trunk 61. At the same time, therefore, no tissue parameter is assigned to the leaves since the leaves form the highest hierarchical level and there would be no possibility of encoding values of a tissue parameter assigned to the leaves.

Alternative depictions for the values of the tissue parameters in the tree structure 60 are also conceivable. For example, it is possible for the thickness of the trunk 61 and/or the thickness of the tree elements to represent the values of the tissue parameters instead of the number of the values of the tissue parameters in value ranges. Accordingly, the construction of the tree structure 60 suggested and illustrated in FIG. 4 should be considered to be only an example, and not restrictive.

Figure 5:
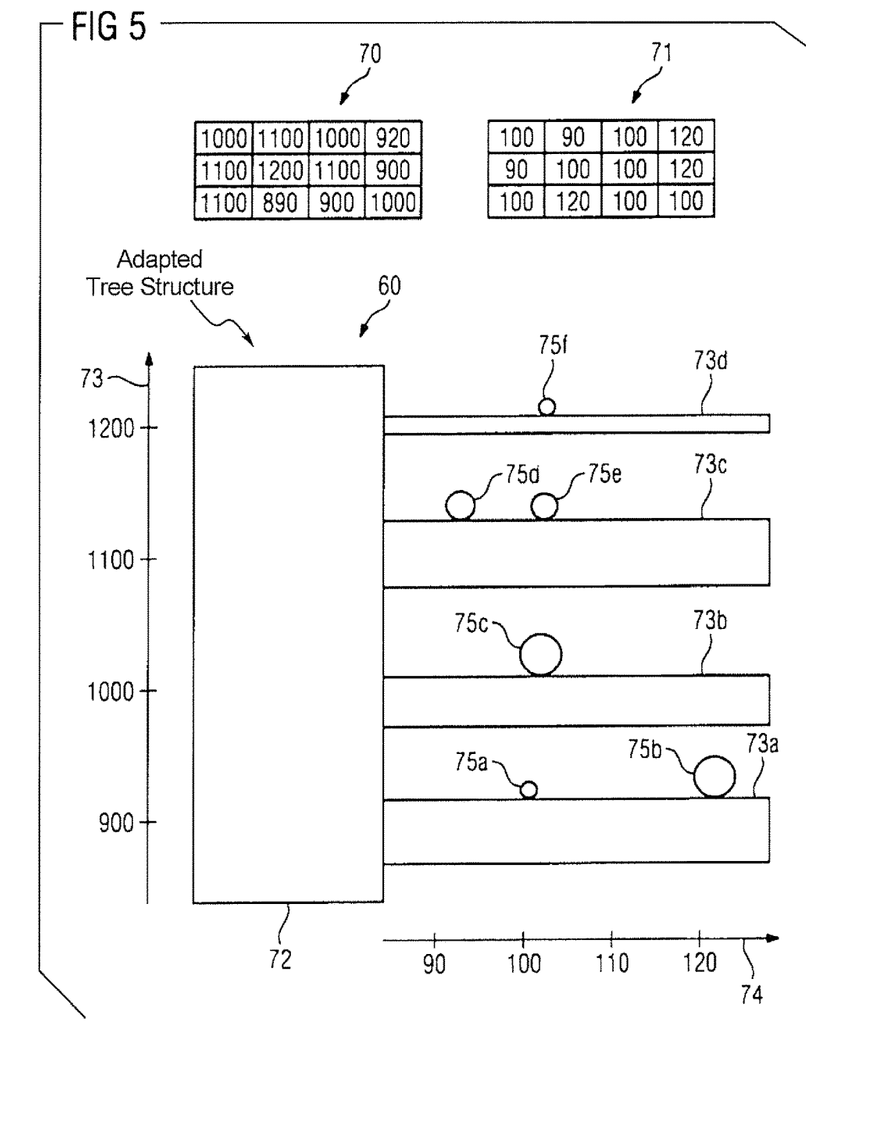
FIG. 5 shows an exemplary tree structure according to the invention together with a specific spatially resolved distribution of values of two tissue parameters which were used to adapt the tree structure to display the values of the two tissue parameters.

FIG. 5 is an exemplary tree structure according to the invention 60 together with a specific spatially resolved distribution of values of two tissue parameters which was used to adapt the tree structure 60 to display the values of the two tissue parameters. FIG. 5 shows an adapted tree structure 60 as could be displayed in this specific case by means of the display monitor 36, for example on an output unit. In this context, the adapted tree structure 60 can be displayed on a user interface. The adapted tree structure 60 can be depicted separately or together with a spatially resolved image display of the magnetic resonance data.

The spatially resolved distribution of the values of the two tissue parameters is shown in the upper region of FIG. 5. These values of the two tissue parameters should only be considered only as an example. At the same time, typical spatially resolved distributions of the tissue parameters comprise a much greater number of data points than is shown in FIG. 5 for purposes of clarity. Accordingly, FIG. 5 is intended only to illustrate the concept behind the adaptation of the tree structure 60 with reference to specific values for the tissue parameters.

FIG. 5 shows an example a first distribution 70 for a first tissue parameter. For purposes of illustration only, the first tissue parameter is intended to be a T1 value, which in given in milliseconds. In this context, the first distribution 70 shown in FIG. 5 has, as an example twelve different T1 values, which were measured in a spatially resolved way in a rectangular grid of 3 times 4. Unlike the display in FIG. 5, in practice, a spatially resolved image display of the T1 values will be in the form of a gray-scale representation or a color display. Here, the first distribution 70 shown in FIG. 5 is repeated once again in the descriptive text in the form of a 3×4 matrix:

| 1000 | 1100 | 1000 | 920 |
| 1100 | 1200 | 1100 | 900 |
| 1100 | 890 | 900 | 1000 |

The same applies to the second distribution 71 shown in FIG. 5 for a second tissue parameter. For purposes of illustration only, the second first tissue parameter is a T2 value. Here, the first distribution 71 shown in FIG. 5 is repeated once again in the descriptive text in the form of a 3×4 matrix:

| 100 | 90 | 100 | 120 |
| 90 | 100 | 100 | 120 |
| 100 | 120 | 100 | 100 |

Corresponding matrix entries for the first distribution 70 and the second distribution 71 are intended to be measured at the same locations in the object under investigation 15. For example, at a location with the x,y coordinates (1,1), there is a T1 value of 1000 ms and a T2 value of 100 ms. At the location with the x,y coordinates (3,3), there is for example a T1 value of 900 ms and a T2 value of 100 ms.

The tree structure 60 depicted in FIG. 5 is now adapted using these specific T1 values and T2 values. Accordingly, it provides a representation of the T1 values and the T2 values.

The tree structure 60 according to FIG. 5 has a trunk 72 and a number of first tree elements 73a, 73b, 73c, 73d, which are arranged on the trunk 72. The T1 values are assigned to the trunk 72, while the T2 values are assigned to the plurality of first tree elements 73a, 73b, 73c, 73d. These assignments can also be made the other way round. A number of second tree elements 75a, 75b, 75c, 75d, 75e, 75f embodied as leaves are arranged on the number of first tree elements 73a, 73b, 73c, 73d and encode the measured T2 values by means of their position or expansion.

In the case shown in FIG. 5, four first value ranges for the T1 values are identified manually or automatically. One lower value range of the four first value ranges includes the T1 values between 850-950 ms, a further value range of the four first value ranges includes the T1 values between 950-1050 ms, a further value range of the four first value ranges includes the T1 values between 1050-1150 ms and a further value range of the four first value ranges includes the T1 values between 1150-1250 ms. Obviously, the limits of the first value ranges could also be set differently or a different number of first value ranges could be used.

Now, in each case a first tree element 73a, 73b, 73c, 73d is assigned to the four first value ranges. For example, a lower first tree element 73a is assigned to the lower value range of the four first value ranges with the T1 values between 850-950 ms. The lower first tree element 73a now encodes the T1 values between 850-950 ms.

In the case shown in FIG. 5, the tree structure 60 is adapted such that a first value scale 73 representing values of the first tissue parameter, i.e. the T1 values, is assigned to the trunk 72. The first value scale 73 can be, but does not have to be, as depicted in the case shown in FIG. 5. It is evident in FIG. 5 that the number of first tree elements 73a, 73b, 73c, 73d are arranged along the first value scale 73 according to the T1 values acquired. For example, the lower first tree element 73a is arranged at the lower end of the first value scale 73.

At the same time, according to FIG. 5, the expansion of the first tree elements 73a, 73b, 73c, 73d should be dependent upon a number of data points in a first distribution 70 with a T1 value lying within the first value range assigned to the respective first tree element 73a, 73b, 73c, 73d. For example, the upper first tree element 73d has the lowest expansion of the four first tree elements 73a, 73b, 73c, 73d, since only one T1 value (x,y coordinates: (2,2)) in the exemplary first distribution 70 lies within in the value range between 1150-1250 ms. At the same time, the lower first tree element 73a has a relatively large expansion since four T1 values in the first distribution 70 lie within the value range between 850-950 ms.

In the case shown in FIG. 5, the data values of the second tissue parameter, i.e. the measured T2 values are encoded by the positioning of the second tree elements 75a, 75b, 75c, 75d, 75e, 75f on the respective first tree elements 73a, 73b, 73c, 73d. Correspondingly, there is also a second value scale 74 for the T2 values, which extends along the first tree elements 73a, 73b, 73c, 73d.

The positioning of a leaf on a first tree element 73a, 73b, 73c, 73d now indicates that there is at least one such T2 value at the respective point of the second value scale 74 in the second distribution 71. The expansion of the leaves can indicate the number of the measured T2 values at the respective point of the second value scale 74. In this way, for example, the expansion of the right leaf 75b at the lower first tree element 73a is greater than the expansion of the left leaf 75a at the lower first tree element 73a since more T2 values of 120 ms are present than T2 values of 100 ms were measured at points in the second distribution 71, which correspond spatially to the points in the first distribution 70 at which T1 values in the value range of 850-950 ms were measured.

FIG. 5 illustrates that the tree structure 60 can reflect combinations of the T1 values and T2 values. For example, only one leaf 75*b* with a T2 value of 120 ms is present at a single first tree 1 element 73*a*. This is due to the fact that in the first distribution 70 only T1 values in the value range between 850-950 ms correspond spatially to the T2 values of 120 ms in the second distribution 71 spatially. There are also four leaves 75*a*, 75*c*, 75*e*, 75*f* arranged on the second value scale am T2 value of 100 ms are arranged. This T2 value of 100 ms was namely measured in spatial correspondence to T1 values from all four value ranges. The uppermost leaf 75*f* represents, for example, the individual measured T1 value from the value range between 1150-1250 ms, since it is arranged on the uppermost first tree element 73*d*. At the same time, the uppermost leaf 75*f* represents the T2 value of 100 ms measured at this location.

Figure 6:
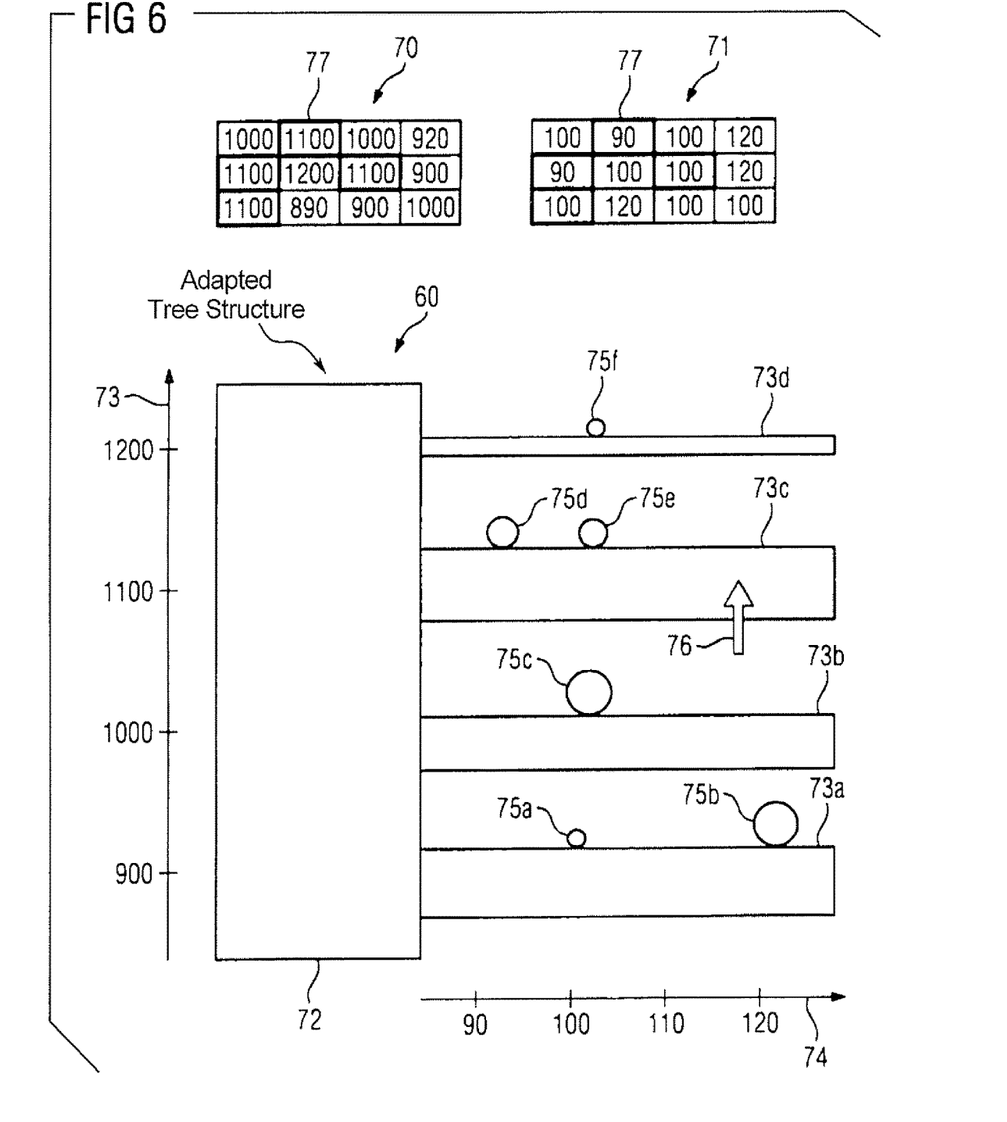
FIG. 6 shows a first exemplary interaction of the user with the tree structure shown in FIG. 5.

FIG. 6 shows a first exemplary interaction of the user with the tree structure 60 shown in FIG. 5.

FIG. 6 shows an alternative embodiment to that shown in FIG. 5. The following description is substantially restricted to the differences from the exemplary embodiment in FIG. 5, wherein reference is made to the description of the exemplary embodiment in FIG. 5 with respect to identical components, features and functions. Substantially identical components, features and functions are generally given the same reference numbers.

FIG. 6 shows now a section of a user interface on which the adapted tree structure 60 according to FIG. 5 is displayed together with a spatially resolved image display of the first distribution 70 of the measured T1 values and the second distribution 71 of the measured T2 values from FIG. 5. Obviously, in practical application, this image display of the first distribution 70 and the second distribution 71 in the practical application will take the form of a gray-scale representation or a color display.

The user is now given the possibility, by an interaction element, in the case shown by a cursor, of interacting with the user interface. In the case shown in FIG. 6, the interaction of the user with the adapted tree structure 60 comprises the selection of a tree element of the tree structure 60, wherein the data points belonging to the tree element are highlighted in the spatially resolved image display of the magnetic resonance data.

In the case depicted, as an example, the user wishes to know which data points of the first distribution 70 and the second distribution 71 are assigned to the second uppermost first tree element 73*c*. This second uppermost first tree element 73*c* encodes, for example, the T1 values lying within in the value range between 1050-1150 ms.

Accordingly, the user selects the second uppermost first tree element 73*c* by clicking the mouse 76. In the spatially resolved image display of the first distribution 70 and the second distribution 71, then the measured T1 values and T2 values belonging to the second uppermost first tree element 73*c* are highlighted by a marking 77, for example a colored marking, by flashing, by magnification or other markings that appear reasonable to those skilled in the art. In the case shown, the measured T1 values belonging to the second uppermost first tree element 73*c* are the T1 values lying in the value range between 1050-1150 ms. In the case shown, the measured T2 values belonging to the second uppermost first tree element 73*c* are the T2 values which were measured at the same position as the highlighted T1 values.

It is also conceivable for the user to select other tree elements of the tree structure 60. If the user selects the trunk 72, in particular all location points of the image display should be highlighted. When the user selects a leaf, for example a leaf arranged on the second uppermost first tree element 73*c*, the number of highlighted location points should be reduced according to the selected T2 values. It is also conceivable for the user to select values along the first scale 73 or the second scale 74.

The procedure illustrated in FIG. 6 offers the user the possibility of selecting conspicuous points in the tree structure 60 and immediately afterward of identifying the associated image points with reference to the marking in the respective conventional image display of the spatially resolved distribution of the tissue parameters.

Figure 7:
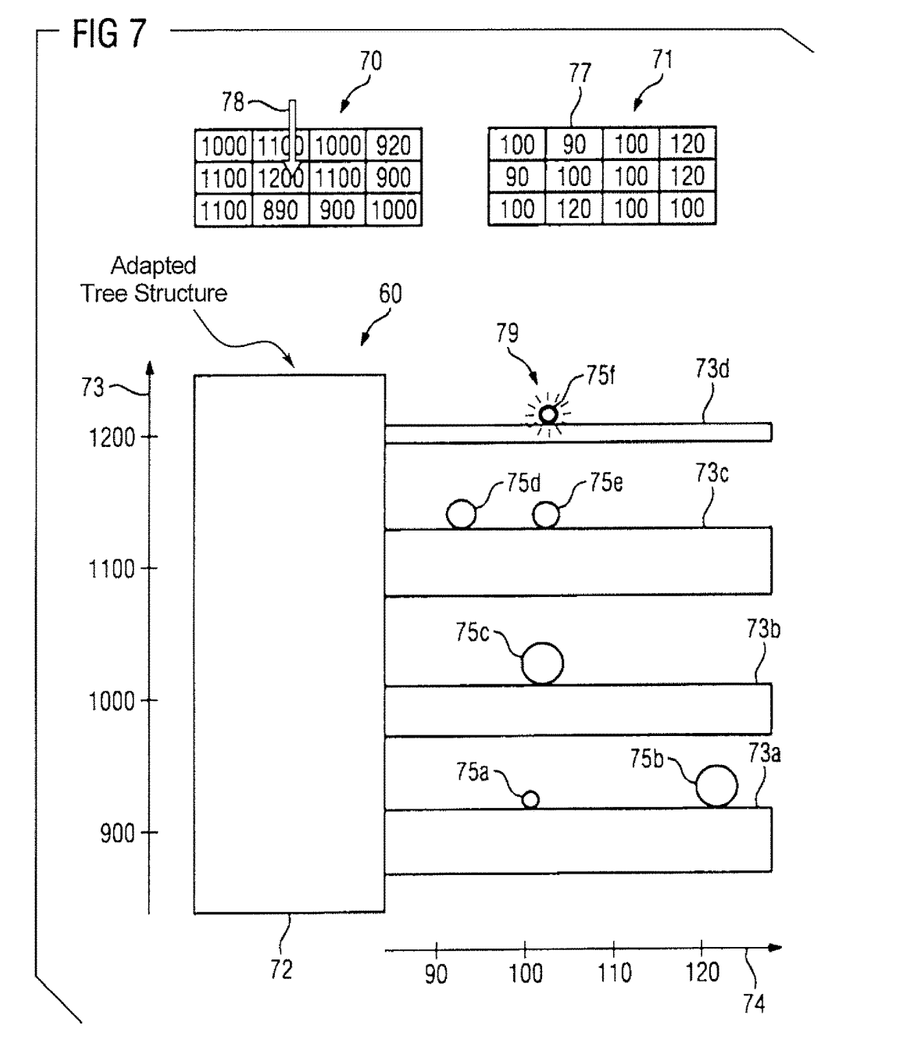
FIG. 7 shows a second exemplary interaction of the user with the tree structure shown in FIG. 5.

FIG. 7 shows a second exemplary interaction of the user with the tree structure 60 shown in FIG. 5.

FIG. 7 shows an alternative embodiment to that shown in the FIG. 5. The following description is substantially restricted to the differences from the exemplary embodiment in FIG. 5, wherein reference is made to the description of the exemplary embodiment in FIG. 5 with respect to identical components, features and functions. Substantially identical components, features and functions are generally given the same reference numbers.

Unlike the case in FIG. 6 in the case shown in FIG. 7, selects the user selects a data point in the spatially resolved image display of the magnetic resonance data on the user interface, wherein a tree element of the tree structure belonging to the data point 60 is highlighted in the adapted tree structure 60.

In the case shown in FIG. 7, the user selects by way of example the data point with the x,y coordinates (2,2) by clicking the mouse 78. A T1 value of 1200 ms and a T2 value of 100 ms were measured at this data point.

The tree element 75*f* belonging to this T1 value of 1200 ms and T2 value of 100 ms is then highlighted in the tree structure 60 by a marking 79. In this context, the highlighting can include the coloring of the tree element 75*f*, the flashing of the tree element 75*f*, a magnification of the tree element 75*f* or another marking of the tree element 75*f* that appears reasonable to those skilled in the art.

For example, the user can recognize how specific spatial anatomical regions in the object under investigation 15 can be represented in the tree structure 60 with reference to the measured values of the tissue parameters.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for visually representing magnetic resonance data, comprising:

providing a processor with magnetic resonance data acquired from a subject, said magnetic resonance data representing a spatially resolved distribution of values of multiple tissue parameters in the subject;

in said processor, creating a tree structure comprising a trunk and a plurality of tree elements that branch from the trunk, and assigning a first tissue parameter, among said multiple tissue parameters, to said trunk, and assigning a second tissue parameter, among said multiple tissue parameters, to said plurality of tree elements;

in said processor, adapting said tree structure with respect to the acquired values of the multiple tissue parameters independently of said spatially resolved distribution, thereby compiling an adapted tree structure; and visually displaying said adapted tree structure at a display monitor in communication with said processor.

2. A method as claimed in claim 1 comprising adapting said tree structure by giving said trunk a value scale comprising a plurality of values of said first tissue parameter, and arranging said plurality of first tree elements along said value scale in accordance with the respective acquired values of said first tissue parameter.

3. A method as claimed in claim 1 comprising defining a first value range of said first tissue parameter, and adapting said tree structure by assigning a first tree element, among said plurality of tree elements, to said first value range.

4. A method as claimed in claim 3 comprising adapting said tree structure by expanding said first tree element dependent on a number of voxels represented by said magnetic resonance data for which the value of the first tissue parameter is within said first value range.

5. A method as claimed in claim 4 comprising adapting said tree structure by setting a position on said trunk, at which said first tree element branches from said trunk, with respect to said first value range.

6. A method as claimed in claim 1 comprising creating said tree structure to give said trunk a thickness, and adapting said tree structure by adapting said thickness of said trunk to represent a number of all of the image points represented by said spatially resolved distribution of values of the multiple tissue parameters.

7. A method as claimed in claim 1 wherein said tree elements are first tree elements, and creating said tree structure with a plurality of second tree elements that branch from said first tree elements.

8. A method as claimed in claim 1 comprising creating said tree structure with said tree elements organized in a hierarchy proceeding from a lowest hierarchical level to a highest hierarchical level, and assigning a specific tissue parameter, among said multiple tissue parameters, to at least one tree element in said highest hierarchical level and creating said tree structure with leaves on said at least one tree element in said highest hierarchical level, with said leaves representing respective values of said specific tissue parameter.

9. A method as claimed in claim 1 comprising displaying said adapted tree structure on a display monitor configured as a user interface allowing user interaction therewith and, in said processor, modifying said adapted tree structure dependent on user interaction via said user interface.

10. A method as claimed in claim 9 comprising receiving in said processor, via said interaction of said user with said adapted tree structure, a selection of tissue parameters to be displayed, among said multiple tissue parameters, and modifying said adapted tree structure dependent on said selection in order to compile a modified adapted tree structure, and displaying said modified adapted tree structure at said display monitor.

11. A method as claimed in claim 9 comprising displaying said adapted tree structure on said user interface together with a spatially resolved image display of said magnetic resonance data.

12. A method as claimed in claim 11 comprising, in said processor, receiving a selection made by said interaction of the user with said adapted tree structure at said user interface, said selection being a selection of a tree element of said tree structure, and, from said processor, causing data points belonging to the selected tree element to be highlighted in said spatially resolved image display of said magnetic resonance data.

13. A method as claimed in claim 12 comprising highlighting said tree element by selecting a data point in said spatially resolved image display of said magnetic resonance data via said user interface, and highlighting the tree element corresponding to said data point.

14. A method as claimed in claim 1 comprising providing said computer with said magnetic resonance data with said distribution of values of said multiple tissue parameters comprising at least one tissue parameter selected from the group consisting of a value for a proton density, a T1 value, a T2 value, a diffusion value, and a value of an extra cellular volume.

15. A computer for visually representing magnetic resonance data, comprising:

a processor provided with magnetic resonance data acquired from a subject, said magnetic resonance data representing a spatially resolved distribution of values of multiple tissue parameters in the subject;

said processor being configured to create a tree structure comprising a trunk and a plurality of tree elements that branch from the trunk, and to assign a first tissue parameter, among said multiple tissue parameters, to said trunk, and to assign a second tissue parameter, among said multiple tissue parameters, to said plurality of tree elements;

said processor being configured to adapt said tree structure with respect to the acquired values of the multiple tissue parameters independently of said spatially resolved distribution, thereby compiling an adapted tree structure;

a display monitor in communication with said processor; and said processor being configured to visually display said adapted tree structure at said display monitor.

16. A magnetic resonance apparatus for visually representing magnetic resonance data, comprising:

a magnetic resonance data acquisition scanner;

a computer configured to operate the magnetic resonance data acquisition scanner in order to acquire magnetic resonance data from a subject in the magnetic resonance data acquisition scanner, said magnetic resonance data representing a spatially resolved distribution of values of multiple tissue parameters in the subject;

a processor provided with said magnetic resonance data;

said processor being configured to create a tree structure comprising a trunk and a plurality of tree elements that branch from the trunk, and to assign a first tissue parameter, among said multiple tissue parameters, to said trunk, and to assign a second tissue parameter, among said multiple tissue parameters, to said plurality of tree elements;

said processor being configured to adapt said tree structure with respect to the acquired values of the multiple tissue parameters independently of said spatially resolved distribution, thereby compiling an adapted tree structure;

a display monitor in communication with said processor; and said processor being configured to visually display said adapted tree structure at said display monitor.

17. A non-transitory, computer-readable data storage medium encoded with programming instructions for visually representing magnetic resonance data, said storage medium being loaded into a processor of a computer that comprises a display monitor in communication with said processor, and said programming instructions causing said processor of said computer to:
- receive magnetic resonance data acquired from a subject, said magnetic resonance data representing a spatially resolved distribution of values of multiple tissue parameters in the subject;
- create a tree structure comprising a trunk and a plurality of tree elements that branch from the trunk, and assign a first tissue parameter, among said multiple tissue parameters independently of said spatially resolved distribution, to said trunk, and assign a second tissue parameter, among said multiple tissue parameters, to said plurality of tree elements;
- adapt said tree structure with respect to the acquired values of the multiple tissue parameters independently of said spatially resolved distribution, thereby compiling an adapted tree structure; and
- visually display said adapted tree structure at a display monitor in communication with said processor.

18. A method for storing magnetic resonance data comprising:
- providing a processor with magnetic resonance data acquired from a subject, said magnetic resonance data comprising a spatially resolved distribution of values of multiple tissue parameters in the subject, said multiple tissue parameters comprising a first tissue parameter and a second tissue parameter, and a first value of said first tissue parameter and a second value of said tissue parameter being assigned to a first item of location information;
- in said processor, creating a data structure comprising a trunk and a plurality of tree elements branching from the trunk, and assigning said first tissue parameter to said trunk and assigning said second tissue parameter to said plurality of tree elements;
- adapting said data structure with respect to the acquired values of said multiple tissue parameters independently of said spatially resolved distribution, thereby compiling an adapted data structure; and
- storing said first item of location information, in a memory in communication with said processor, at a point in said adapted tree structure in said memory that is defined with respect to said first value of said first tissue parameter and said second value of said second tissue parameter.

* * * * *